United States Patent
Uratani

(10) Patent No.: US 9,513,268 B2
(45) Date of Patent: Dec. 6, 2016

(54) ANALYSIS SYSTEM AND MANAGEMENT DEVICE

(71) Applicant: HORIBA, Ltd., Kyoto (JP)

(72) Inventor: Katsumi Uratani, Kyoto (JP)

(73) Assignee: Horiba, Ltd., Kyoto (JP)

( * ) Notice: Subject to any disclaimer, the term of this patent is extended or adjusted under 35 U.S.C. 154(b) by 476 days.

(21) Appl. No.: 14/074,031

(22) Filed: Nov. 7, 2013

(65) Prior Publication Data

US 2014/0129153 A1    May 8, 2014

(30) Foreign Application Priority Data

Nov. 7, 2012  (JP) ................................. 2012-245083

(51) Int. Cl.
  *G01N 33/00* (2006.01)
  *G01N 1/22* (2006.01)
  *G01N 35/00* (2006.01)

(52) U.S. Cl.
  CPC ........ *G01N 33/0073* (2013.01); *G01N 1/2252* (2013.01); *G01N 33/0062* (2013.01); *G01N 35/00871* (2013.01)

(58) Field of Classification Search
  CPC .............. G01N 33/0073; G01N 1/2252; G01N 35/00871; G01N 33/0062
  USPC .................... 702/22; 709/201, 221, 232, 220
  See application file for complete search history.

(56) References Cited

U.S. PATENT DOCUMENTS

| | | | |
|---|---|---|---|
| 7,167,844 B1 * | 1/2007 | Leong | G06Q 30/04 705/37 |
| 8,095,627 B2 * | 1/2012 | Izaki | G06F 3/1204 709/220 |
| 2003/0225472 A1 | 12/2003 | Kato | |
| 2005/0223008 A1 * | 10/2005 | Kubota | G06F 21/40 |
| 2006/0288116 A1 * | 12/2006 | Seki | H04L 63/20 709/232 |
| 2007/0043805 A1 * | 2/2007 | Izaki | G06F 3/1204 709/201 |
| 2009/0119765 A1 * | 5/2009 | Sakayama | G06F 21/33 726/10 |

FOREIGN PATENT DOCUMENTS

| | | |
|---|---|---|
| JP | 08-103739 | 4/1996 |
| JP | 11-031019 | 2/1999 |
| JP | 2002-229538 | 8/2002 |
| JP | 2003-273577 | 9/2003 |
| JP | 2005-327080 | 11/2005 |
| JP | 2007-003900 | 1/2007 |
| JP | 2008-112968 | 5/2008 |
| JP | 4303492 B | 7/2009 |
| JP | 2010-231473 | 10/2010 |

OTHER PUBLICATIONS

Office Action dated Mar. 15, 2016 issued in Chinese patent application No. 201310538049.8, 14 pages.

\* cited by examiner

*Primary Examiner* — Carol S Tsai

(74) *Attorney, Agent, or Firm* — Brooks Kushman P.C.

(57) ABSTRACT

This invention is to make it possible for the analysis system to conduct the minimum operation of the management device or monitoring a movement of the analysis device continuously while preventing an unexpected operation by an unauthorized user. In order to attain this object, the access level is automatically changed to the smaller operable range in case that the operation conducted based on a certain access level is interrupted for a certain period of time.

5 Claims, 3 Drawing Sheets

FIG. 3

ANALYSIS SYSTEM AND MANAGEMENT DEVICE

CROSS-REFERENCE TO RELATED APPLICATION

This application claims priority to JP Application No. 2012-245083, filed Nov. 7, 2012, the disclosure of which is incorporated in its entirety by reference herein.

FIELD OF THE ART

This invention relates to an analysis system comprising one or more analysis devices that analyze an exhaust gas of an internal combustion engine and a management device that manages the analysis devices.

BACKGROUND ART

Conventionally, as shown in the paragraph 0048 of Publication of Applications No. 4303492, for this kind of the analysis devices that require various settings, correction, operations for preparation, maintenance or the like, an access level is divided into a plural number and an operable range is determined according to the access level by specifying the access level by an ID or a password. This is because contingency might be generated such that data is falsified or eliminated or a malfunction or breakage of the analysis device due to the usage of an immature user if all operations concerning the analysis device are allowed equally for any users.

DISCLOSURE OF THE INVENTION

Problems to be Solved by the Invention

However, if a user whose access level is high leaves his or her seat in front of a console without logging-off, it is possible for an unspecified third person to conduct an operation so that the same problem as the above-mentioned problem might be generated.

Then, similar to a personal computer, it can be conceived that the window is returned to a log in window and the operation is prohibited without logging in again after the operation is interrupted for a certain period of time. However, it is important for the analysis system to make the operation status of each analysis device visible on a constant basis. Then, even if it is temporarily, it is not preferable that the operation status is invisible and incapable of being conducted.

The present claimed invention is made with considering this situation, and intends to solve all of the problems and a main object of this invention is to make it possible to conduct the minimum operation of the management device or to monitor the behavior of the analysis device continuously while preventing an unexpected operation by an unauthorized user.

Means to Solve the Problems

More specifically, the analysis system in accordance with the present claimed invention comprises one or more analysis devices and a management device that manages the analysis devices, and is characterized by that the management device recognizes a user based on input user information and sets an operable range for the management device of the user in an initial operable range previously determined for each of the users, and in case that an operation of the user is interrupted for a certain period of time, the operable range of the user is automatically changed to a previously determined base operable range.

The operation described above is opening/closing a window of the management device, a command input to the analysis device, an input of various settings or a command of printing. In addition, the base operable range described above is an operable range wherein the minimum operation or the movement monitoring to the management device or the analysis device can be conducted.

More specifically, it is preferable that the management device comprises an access level memory part that memorizes a plurality of access levels whose initial operable range for the management device is determined respectively and users who are allowed for each of the access levels and an operable range setting part that recognizes the user based on the input user information, specifies the access level that is set for each of the users by referring to the access level memory part and sets the operable range for the management device of the user in the initial operable range that is determined for the access level, and in case that the operation conducted based on one access level is interrupted for a certain period of time, the operable range setting part automatically changes the access level to a base access level as being an access level whose base operable range is determined.

In order to make it possible more securely to prevent a contingency such as an improper operation or breakage of the analysis device, it is preferable to set the base access level in the access level of the minimum operable range by the operable range setting part.

In case that an item that is required to be monitored continuously or whose situation is required to be grasped continuously is displayed on a window, even though the item is not allowed to be monitored by a user of a low ranking level (a user whose operable range is smaller), it may be so configured that the item is displayed as it is even after the operable range is automatically changed to the base operable range unless an erase operation is conducted. In this case, it is necessary to lock the window so as not to be operated by the user of the low ranking level.

In order to prevent the operation unnecessarily from being complicated, it is preferable that, in case that a given execution command such as initiation of a measurement or initiation of correction is instructed to the analysis device, the operable range setting part automatically changes the operable range of the user to the base operable range unless the operation is conducted for a certain period of time after the completion of the execution command by the analysis device.

Effect of the Invention

In accordance with the arrangement of this invention, when a certain period of time passes after a high ranking level user whose operable range is big leaves a console without logging-off, the operable range is automatically lowered to the base operable range so that it is not possible to conduct an operation of importance whose access level is set for the high ranking level user, thereby preventing an unexpected operation by an unauthorized user.

Meanwhile, since a base operation that is allowed for a low ranking level user is secured continuously without performing log-in again, it is possible to obtain an effect that a minimum operation of the management device or monitoring a movement of the analysis device can be conducted on a constant basis.

BRIEF DESCRIPTION OF THE DRAWINGS

FIG. 3 is a display configuration diagram showing one embodiment of a window displayed in this embodiment.

DETAILED DESCRIPTION

Modes for Carrying Out the Invention

One embodiment of this invention will be explained with reference to drawings.

Figure 1:
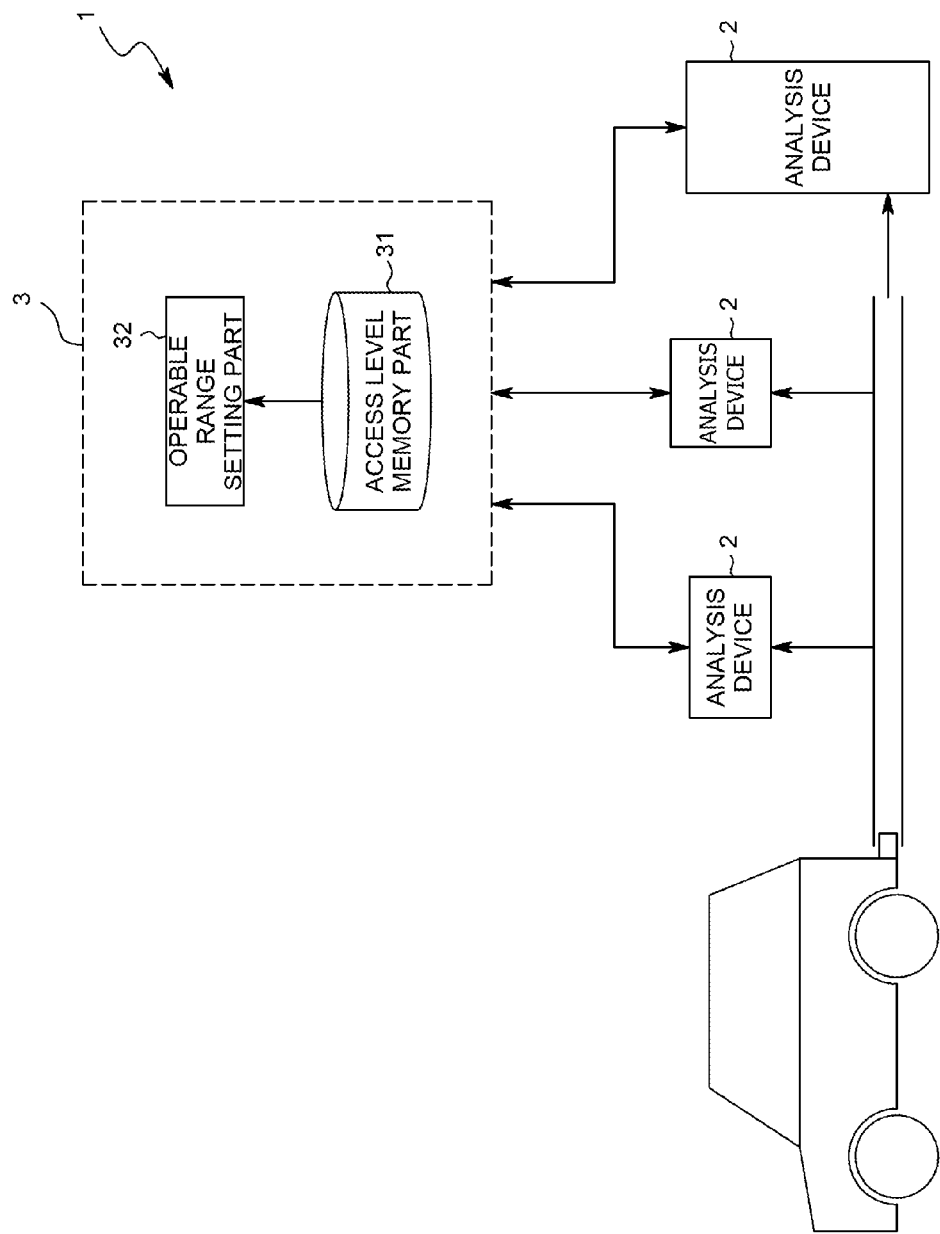
FIG. 1 is an overall configuration diagram of an analysis system in accordance with one embodiment of this invention.

An analysis system 1 in accordance with this embodiment is, as shown in FIG. 1, for sampling an exhaust gas of an internal combustion engine of a vehicle and analyzing/calculating a component concentration, a fuel efficiency or an EGR ratio of the exhaust gas, and comprises a plurality of exhaust gas analysis devices 2 (for example, a CVS device, an EGR ratio measurement device or an exhaust gas comprehensive analysis device inside of which a plurality of exhaust gas analysis units are provided) and a management device 3 that comprehensively manages these analysis devices 2 by transmitting an operation command to each of the analysis devices 2, conducting settings or calibrating or receiving measured data.

In this embodiment, the management device 3 divides the access level of the user into a plural number, and in case that an operation of the management device 3 by the user is not conducted for a certain period of time (hereinafter also called as a permission time), the access level is automatically lowered to the minimum level as being a base access level.

Then various functions of the management device 3 in accordance with this access level will be explained.

The management device 3 physically comprises a CPU, a memory, a communication device, a display and an input device (a mouse or a keyboard or the like). The management device 3 produces functions as an access level memory part 31 and an operable range setting part 32 by cooperating with the CPU and its peripheral devices based on predetermined programs stored in the memory.

The access level memory part 31 stores a plurality of access levels to determine an operable range for the management device 3 and users who are allowed to access each of the access levels.

In this embodiment, for example, six access levels, namely, "Operator", "Supervisor", "Administrator", "Service", "Manufacture" and "Developer" are set in an ascending order from the lowest level. Both the operable range and a user identifier for identifying the user are assigned to each of the access levels.

The operable range setting part 32 recognizes the user based on the user information (in this embodiment, the user identifier and a pass word) input by the user on a log-in window, not shown in drawings, specifies the access level set for the user by referring to the access level memory part 31 and sets the operable range determined for the access level.

Furthermore, in this embodiment, in case that an operation (for example, open/close the window screen, input of executing a command or various setting for the analysis device, or an operation of printing) on a console conducted based on a certain access level is interrupted for a certain period of time, the access level is automatically changed to the "Operator" level as being the access level of the minimum operable range. For example, the range that the user of the "Operator" level is allowed to operate is an operation range in accordance with an ordinary movement/usage of this analysis system such as a preparation, operation and cleaning up of the test (a measurement by the analysis devices or equipment operation such as dynamo of the vehicle test facility) in addition to starting up or halting the analysis devices or the management devices (or whole of vehicle test equipment including the analysis devices). Meanwhile, for example, in the "Supervisor" level, the management of this analysis system, namely, periodic maintenance, a diagnosis, or an adjustment can be operated.

Next, an example of the movement of this management device 3 will be explained.

Figure 2:
FIG. 2 is a display configuration diagram showing one embodiment of a window displayed in this embodiment.

The management device 3 has a function of indicating each of the total operating time of various devices constituting the analysis device 2 and a function of issuing a warning when the total operating time exceeds an allowable time that is determined for each device or the total operating time approaches the allowable time, and these functions are produced when a window (a prevention protection window) W1 as shown in FIG. 2 is opened.

The prevention protection window W1 displays, for example, a device name, a present total operating time, an allowable time, a remaining time for each device in a list form. When the remaining time approaches zero, the remaining time is displayed and a warning is issued. In addition, a reset button B1 and a detail button B2 are arranged for each device. When the reset button B1 is clicked, it is possible to reset the total operating time of the device to zero. When the detail button B2 is clicked, a detail setting window, not shown in drawings, opens separately so that it becomes possible to change the setting of the allowable time or the warning timing.

It is possible for the user of the "Operator" level to see the total operating time of each device by opening the prevention protection window W1, however, it is not possible for the user of the "Operator" level to operate the reset button B1 and the detail button B2 due to the restriction by the operable range setting part 32. For example, the reset button B1 and the detail button B2 are not displayed or are displayed in a light character so as not to be capable of clicking.

Meanwhile, for example, the user of the "Administrator" level can operate the reset button B1 and cannot operate the detail button B2.

The user of the "Service" level or over can operate both of the reset button B1 and detail button B2, and can change each setting in the detail setting window.

Then, when a permission time passes while the user of the "Service" level or over does not conduct any operation in a state that the prevention protection window W1 is open, the operable range setting part 32 is activated so that the access level is automatically lowered to the "Operator" level and the operation to the reset button B1 and the detail button B2 is prohibited.

Figure 3:
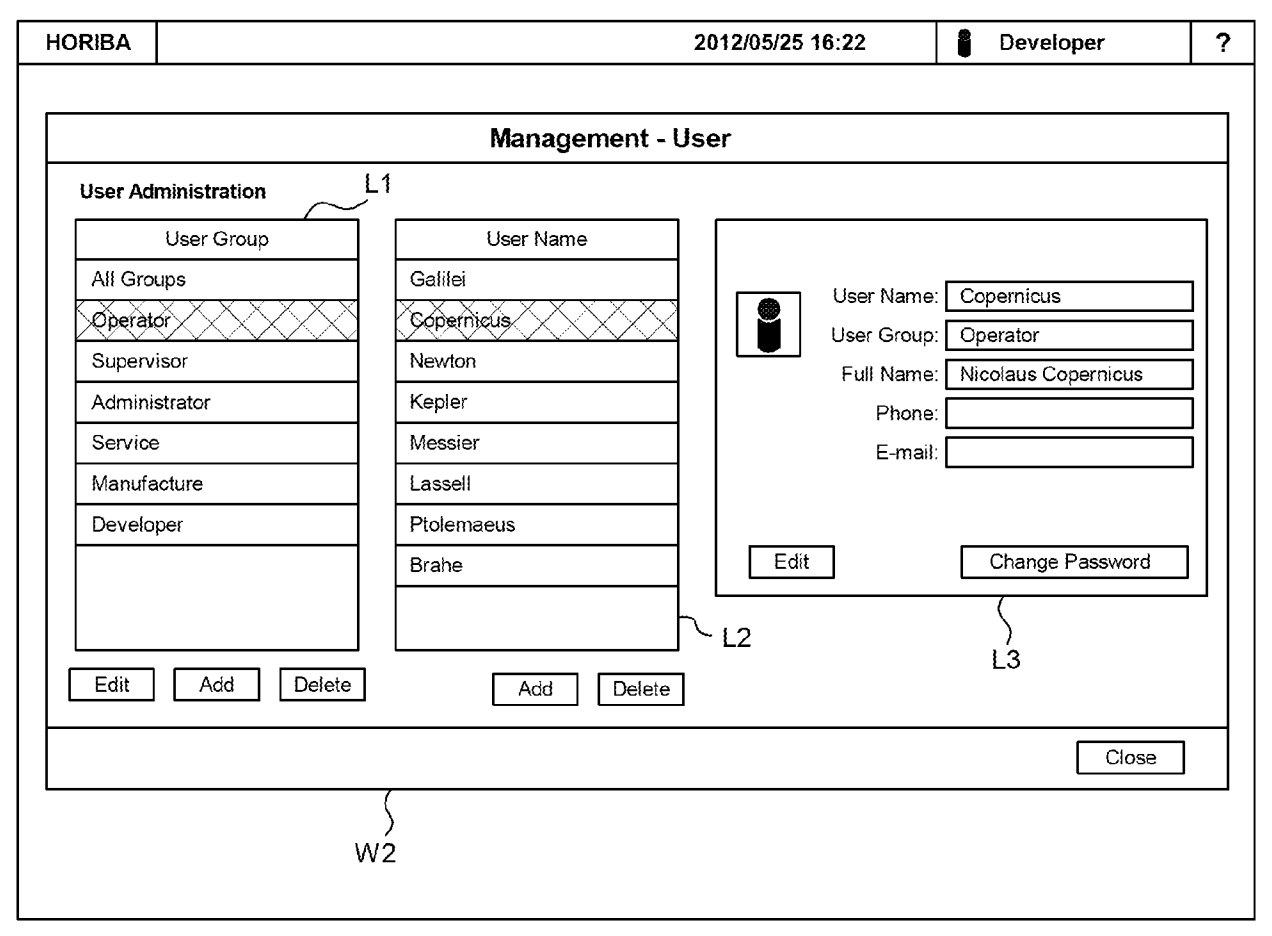

Another example will be presented. The management device 3 makes it possible for the user of the "Developer" level as being the highest level to open the user setting window W2 shown in FIG. 3 and to change the access level of each user or the user information.

The access level is displayed on a list section L1 and the user name that belongs to the access level selected in the list section L1 is displayed on a list section L2. Since the detailed information on the user selected on the list section L2 is displayed on a user information section L3, it is possible for the user of the "Developer" level to change the access level of the user and the user information by editing the user information section L3.

When a permission time passes without any operation in a state that the user setting window W2 is open, the access level is automatically lowered to the "Operator" level so that any operation is not allowed except for the "Close" operation of the window W2 although the user setting window W2 is displayed.

In addition, when the window W2 is once closed after the access level is automatically lowered, it is not possible to open the window W2 any more while the authority of the access level is still that of the "Operator" level.

Further different example will be presented. For example, various buttons or tabs are set on an analysis data display window, not shown in drawings, where analysis results are displayed one after another. A predetermined button or tab among the displayed buttons or tabs can be used only by a user whose access level is equal to or higher than a predetermined access level. When the access level is automatically lowered, these buttons and tabs cannot be operated or these buttons and tabs are not displayed.

In accordance with this embodiment, when a certain period of time passes after the user of a high ranking access level leaves a console without logging-off, the access level is automatically lowered to the lowest access level so that it is not possible to conduct an operation of importance whose access level is set as the high ranking access level, thereby preventing an unexpected operation by an unauthorized user.

Meanwhile, since the operation of the user whose access level is the lowest is secured continuously without performing log-in again, it is possible to obtain an effect that a minimum operation of the management device or monitoring a movement of the analysis device can be conducted on a constant basis.

The present claimed invention is not limited to the above-mentioned embodiment.

For example, the operable range of each user is classified into a plurality of the access levels and each user belongs to either of the access levels in the above-mentioned embodiment, however, the operable range that is allowed for each user, namely an initial operable range in claims may be set without using a concept as the access level.

More concretely, the initial operable range assigned to each user is stored in an initial operable range memory part (not shown in drawings) set in the memory. In addition, the base operable range as being the operable range corresponding to the operable range of the lowest access level is previously specified and stored in a base operable range memory part (not shown in drawings) set in the memory.

Then, at a time when the user logs in, the operable range setting part sets the operable range of the user as the initial operable range assigned to the user by referring to the initial operable range memory part. Meanwhile, in case that the operation by the user is interrupted for a certain period of time, the operable range of the user is automatically changed to the base operable range.

In accordance with this arrangement, it is possible to set the initial operable range for each user more finely.

In addition, at a time when the user of the high ranking access level opens a window that is not allowed for the user of the lowest access level to open and a permission time passes, the window may be automatically closed. Originally, from the viewpoint of monitoring, the window that is not allowed for the user of the lowest access level to open is unnecessary.

The permission time may be varied in accordance with each function or each access level. It can be conceived that the permission time is set shorter for the higher importance wherein it is not assumed to be operated by the user of the low ranking access level.

For an operation execution command to the analysis device, a waiting period without requiring any operation might be generated after inputting the command until the operation of the analysis device is completed. For example, a waiting period is generated from a time when the correction command is inputted to a time of completing the correction. During this waiting period, if the access level is automatically lowered because the permission period passes, it becomes necessary to log in again after the waiting period, thereby complicating the operation. Then, in this case, permission period may start after completion of the waiting period.

It is not necessarily to lower the access level to the lowest level after the permission period passes, the access level may be lowered one by one. In other words, the base access level is not necessarily the lowest access level and may vary according to time. The base access level may be set as the access level of the ranking higher than the lowest level depending on a practicing mode of the analysis system. The same applies also to the base operable range.

The present claimed invention is not limited to the above-mentioned embodiment and may be variously modified without departing from a spirit of the invention.

EXPLANATION OF CODES

1 . . . analysis system
2 . . . analysis device
3 . . . management device
31 . . . access level memory part
32 . . . operable range setting part

What is claimed is:

1. An analysis system comprising:
one or more analysis devices and a management device that manages the analysis devices, wherein
the management device recognizes a user based on input user information and sets an operable range for the management device of the user in an initial operable range previously determined for each of the users, and in case that an operation of the user is interrupted for a certain period of time, the operable range of the user is automatically changed to a previously determined base operable range, and
the management device comprises
an access level memory part that memorizes a plurality of access levels whose initial operable range is determined respectively and users who are allowed for each of the access levels, and
an operable range setting part that
recognizes the user based on the input user information,
specifies the access level that is set for each of the users by referring to the access level memory part, sets the operable range for the management device of the user in the initial operable range that is determined for the access level, and in case that the operation conducted based on one access level is interrupted for a certain period of time, automatically changes the access level to a base access level as being an access level whose base operable range is determined.

2. The analysis system described in claim 1, wherein the base access level is the access level of the minimum operable range.

3. The analysis system described in claim 1, wherein in case that the operable range is changed, the operable range setting part displays a window just prior to the change as it is unless an erase operation is conducted.

4. The analysis system described in claim 1, wherein in case that a given execution command such as initiation of a measurement or initiation of correction is instructed to the analysis device, the operable range setting part automatically changes the operable range of the user to the base operable range unless the operation is conducted for a certain period of time after completion of the execution by the analysis device.

5. A management device that manages one or more analysis devices, wherein a user is recognized based on input user information, an operable range for the management device of the user is set in an initial operable range that is previously determined for each of the users, and in case that an operation of the user is interrupted for a certain period of time, the operable range of the user is automatically changed to a previously determined base operable range, and the management device comprises an access level memory part that memorizes a plurality of access levels whose initial operable range is determined respectively and users who are allowed for each of the access levels, and an operable range setting part that recognizes the user based on the input user information, specifies the access level that is set for each of the users by referring to the access level memory part, sets the operable range for the management device of the user in the initial operable range that is determined for the access level, and in case that the operation conducted based on one access level is interrupted for a certain period of time, automatically changes the access level to a base access level as being an access level whose base operable range is determined.

* * * * *